United States Patent
Gliner et al.

(10) Patent No.: US 6,208,898 B1
(45) Date of Patent: Mar. 27, 2001

(54) IMPEDANCE ESTIMATION WITH DYNAMIC WAVEFORM CONTROL IN AN ELECTROTHERAPY APPARATUS

(75) Inventors: Bradford E. Gliner, Issaquah; Thomas D. Lyster, Bothell, both of WA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/277,381

(22) Filed: Mar. 25, 1999

(51) Int. Cl.$^7$ .................................................. A61N 1/39
(52) U.S. Cl. ..................................... 607/8; 607/62
(58) Field of Search ..................... 607/62, 63, 8

(56) References Cited

U.S. PATENT DOCUMENTS

| | | |
|---|---|---|
| 3,747,605 | 7/1973 | Cook . |
| 4,328,808 | 5/1982 | Charbonnier et al. . |
| 4,840,177 | 6/1989 | Charbonnier et al. ............... 128/419 |
| 5,111,813 | 5/1992 | Charbonnier et al. ............... 128/419 |
| 5,593,427 | 1/1997 | Gliner et al. ............................ 607/7 |
| 5,601,612 | 2/1997 | Gliner et al. ............................ 607/7 |
| 5,607,454 | 3/1997 | Cameron et al. ....................... 607/5 |
| 5,620,470 | 4/1997 | Gliner et al. ............................ 607/7 |
| 5,735,879 | 4/1998 | Gliner et al. ............................ 607/7 |
| 5,836,977 | 11/1998 | Myers . |
| 5,836,978 | 11/1998 | Gliner et al. . |

FOREIGN PATENT DOCUMENTS

| | | |
|---|---|---|
| 0246064 | 11/1987 | (EP) . |
| WO98/47563 | 10/1998 | (WO) .............................. A61N/1/39 |

Primary Examiner—William E. Kamm

(57) ABSTRACT

An electrotherapy apparatus performs a low level impedance measurement upon the patient to determine the initial charge level on the capacitor used to deliver an electrotherapy waveform to the patient. In addition, the waveform applied to the patient is dynamically controlled to compensate for patient impedance variability. Determining the initial charge level in this manner prevents unnecessarily high peak currents from flowing in low impedance patients while maintaining peak current in high impedance patients at therapeutically beneficial levels. The electrotherapy apparatus includes a measuring device used for measuring a parameter related to the impedance of the patient. The parameter is used for determining low level patient impedance. The measuring device provides a voltage output used by a controller for determining the initial charge level of the capacitor. A first embodiment of a first electrotherapy apparatus includes four electronic switches to deliver a bi-phasic waveform to the patient. The first embodiment of the first electrotherapy apparatus further includes a comparator coupled to a timer to monitor the voltage across the capacitor and control the termination or extension of the waveform applied to the patient. A first embodiment of a second electrotherapy apparatus measures the charge delivered to the patient and sets the time of the first phase of the bi-phasic pulse based upon the time required to deliver a predetermined amount of charge to the patient.

34 Claims, 9 Drawing Sheets

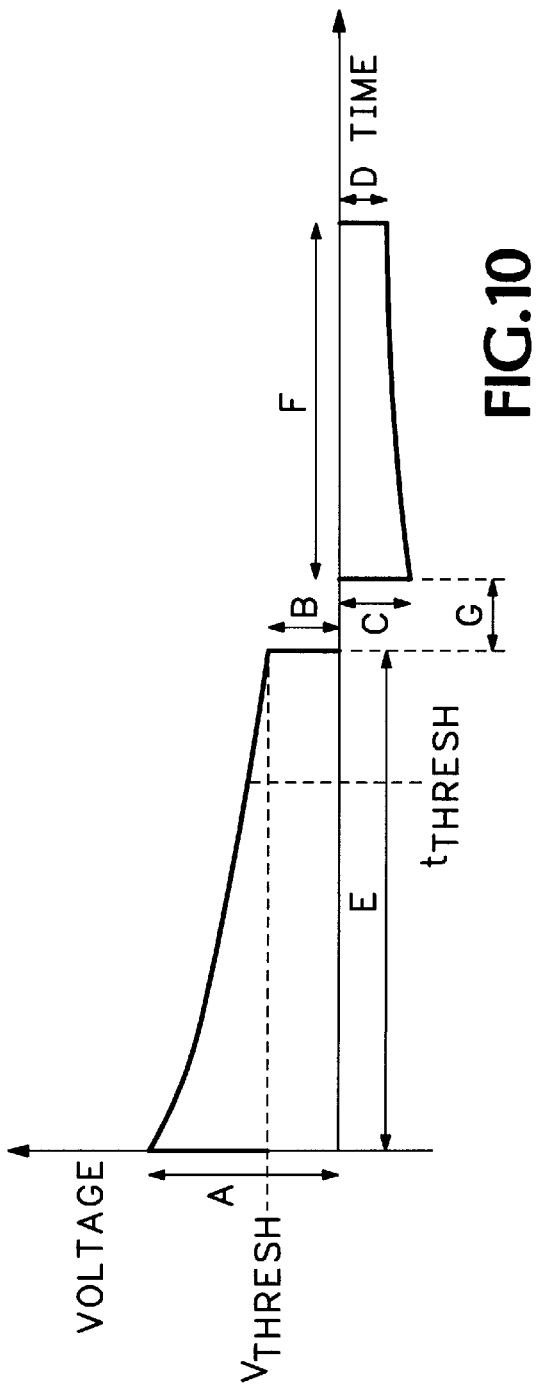
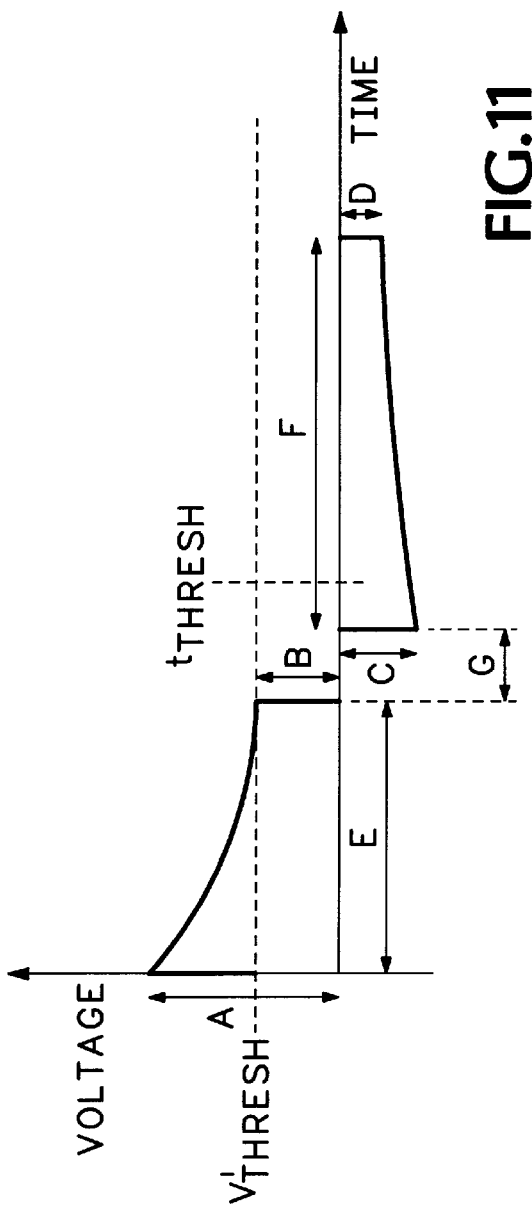

IMPEDANCE ESTIMATION WITH DYNAMIC WAVEFORM CONTROL IN AN ELECTROTHERAPY APPARATUS

FIELD OF THE INVENTION

This invention relates generally to an electrotherapy method and apparatus for delivering an electrotherapy waveform to a patient's heart. In particular, this invention relates to a method and apparatus to deliver an electrotherapy waveform to a patient's heart through electrodes attached to the patient.

BACKGROUND OF THE INVENTION

Defibrillators apply pulses of electricity to a patient's heart to convert ventricular arrhythmias, such as ventricular fibrillation and ventricular tachycardia, to normal heart rhythms through the processes of defibrillation and cardioversion, respectively. There are two main classifications of defibrillators: external and implanted. Implantable defibrillators are surgically implanted in patients who have a high likelihood of needing electrotherapy in the future. Implanted defibrillators typically monitor the patient's heart activity and automatically supply electrotherapeutic pulses directly to the patient's heart when indicated. Thus, implanted defibrillators permit the patient to function in a somewhat normal fashion away from the watchful eye of medical personnel.

External defibrillators send electrical pulses to the patient's heart through electrodes applied to the patient's torso. External defibrillators are useful in the emergency room, the operating room, emergency medical vehicles or other situations where there may be an unanticipated need to provide electrotherapy to a patient on short notice. The advantage of external defibrillators is that they may be used on a patient as needed, then subsequently moved to be used with another patient. However, because external defibrillators deliver their electrotherapeutic pulses to the patient's heart indirectly (i.e., from the surface of the patient's skin rather than directly to the heart), they must operate at higher energies, voltages and/or currents than implanted defibrillators.

The time plot of the current or voltage pulse delivered by a defibrillator shows the defibrillator's characteristic waveform. Waveforms are characterized according to the shape, polarity, duration and number of pulse phases. Most current external defibrillators deliver monophasic current or voltage electrotherapeutic pulses, although some deliver biphasic sinusoidal pulses. Some prior art implantable defibrillators, on the other hand, use truncated exponential, biphasic waveforms. Examples of biphasic implantable defibrillators may be found in U.S. Pat. No. 4,821,723 to Baker, Jr., et al.; U.S. Pat. No. 5,083,562 to de Coriolis et al.; U.S. Pat. No. 4,800,883 to Winstrom; U.S. Pat. No. 4,850,357 to Bach, Jr.; and U.S. Pat. No. 4,953,551 to Mehra et al. Because each implanted defibrillator is dedicated to a single patient, its operating parameters, such as electrical pulse amplitudes and total energy delivered, may be effectively titrated to the physiology of the patient to optimize the defibrillator's effectiveness. Thus, for example, the initial voltage, first phase duration and total pulse duration may be set when the device is implanted to deliver the desired amount of energy or to achieve the desired start and end voltage differential (i.e., a constant tilt).

In contrast, because external defibrillator electrodes are not in direct contact with the patient's heart, and because external defibrillators must be able to be used on a variety of patients having a variety of physiological differences, external defibrillators must operate according to pulse amplitude and duration parameters that will be effective in most patients, no matter what the patient's physiology. For example, the impedance presented by the tissue between external defibrillator electrodes and the patient's heart varies from patient to patient, thereby varying the intensity and waveform shape of the electrotherapy waveform actually delivered to the patient's heart for a given initial pulse amplitude and duration. Pulse amplitudes and durations effective to treat low impedance patients do not necessarily deliver effective and energy efficient treatments to high impedance patients.

A continuing challenge in applying an optimal electrotherapy waveform to the patient is to compensate for patient to patient impedance variations with the application of the initial electrotherapy waveform. A need exists for a defibrillation method and apparatus which will permit the delivery of an optimal electrotherapy waveform on the initial as well as subsequent applications of electrotherapy waveforms.

SUMMARY OF THE INVENTION

Accordingly, in an electrotherapy apparatus including an energy source, a method for applying electrotherapy to a patient includes measuring a first parameter relating to an impedance of the patient and configuring the energy source based upon the first parameter. The method further includes coupling the energy source to the patient and measuring a third parameter related to energy delivered to the patient by the energy source. The method also includes decoupling the energy source from the patient based upon the third parameter.

An electrotherapy apparatus for performing electrotherapy on a patient through a first electrode and a second electrode includes an energy source to deliver energy to the patient through the first electrode and the second electrode. The electrotherapy apparatus further includes a sensor configured to measure a first parameter related to the energy delivered to the patient. Additionally, included in the electrotherapy apparatus is a first connecting mechanism configured to couple and decouple the energy source to and from, respectively, the first electrode and the second electrode. The electrotherapy apparatus also includes a measuring device configured to measure a second parameter, that varies with patient impedance, through the first electrode and the second electrode. The electrotherapy apparatus further includes a controller coupled to the first connecting mechanism and the energy source and arranged to receive the first parameter from the sensor. The controller is configured to actuate the first connecting mechanism to couple the energy source to the first electrode and the second electrode. The controller is also configured to actuate the first connecting mechanism to decouple the energy source from the first electrode and the second electrode based upon the first parameter. The controller is arranged to receive the second parameter from the measuring device to configure the energy source based upon the second parameter.

A defibrillator for delivering a multi-phasic waveform through a first electrode and a second electrode to a patient for defibrillation includes a capacitor for storing charge for delivery to the patient through the first electrode and the second electrode. The capacitor includes a first terminal and a second terminal. The defibrillator also includes a power supply for charging the capacitor. The defibrillator further includes a first connecting mechanism coupled between the first terminal and the second terminal of the capacitor and the first electrode and the second electrode to permit the first terminal of the capacitor to couple and decouple to and from one of the first electrode and the second electrode. The first connecting mechanism also permits the second terminal of the capacitor to couple and decouple to and from one of the first electrode and the second electrode. The defibrillator also includes a sensor for measuring a first parameter related to the energy supplied by the capacitor. The defibrillator further includes a circuit to measure a second parameter that varies with patient impedance. The circuit is configured for measuring the second parameter through the first electrode and the second electrode. The defibrillator also includes a controller coupled to the first connecting mechanism and arranged to receive the first parameter. The controller is configured to actuate the first connecting mechanism to decouple the first terminal and the second terminal of the capacitor from the first electrode and the second electrode based upon the first parameter. The controller is arranged to receive the second parameter from the measuring device and to configure the power supply for charging the capacitor based upon the second parameter.

BRIEF DESCRIPTION OF THE DRAWINGS

A more thorough understanding of the invention may be had from the consideration of the following detailed description taken in conjunction with the accompanying drawings in which:

FIG. 10 shows a typical waveform that could result by dynamically adjusting the waveform applied to a high impedance patient.

FIG. 11 shows a typical waveform that could result by dynamically adjusting the waveform applied to a low impedance patient.

DETAILED DESCRIPTION OF THE DRAWINGS

The present invention is not limited to the specific exemplary embodiments illustrated in this specification. Although the electrotherapy apparatus will be discussed in the context of operation external to a patient, it should be recognized that the disclosed principles are adaptable to an electrotherapy apparatus which operates internal to the patient. In addition, although the electrotherapy apparatus will be discussed in the context of the application of a bi-phasic pulse, it should be recognized that the disclosed principles are adaptable to an electrotherapy apparatus which applies other waveshapes, such as mono-phasic or damped sinusoid waveshapes.

Figure 1:
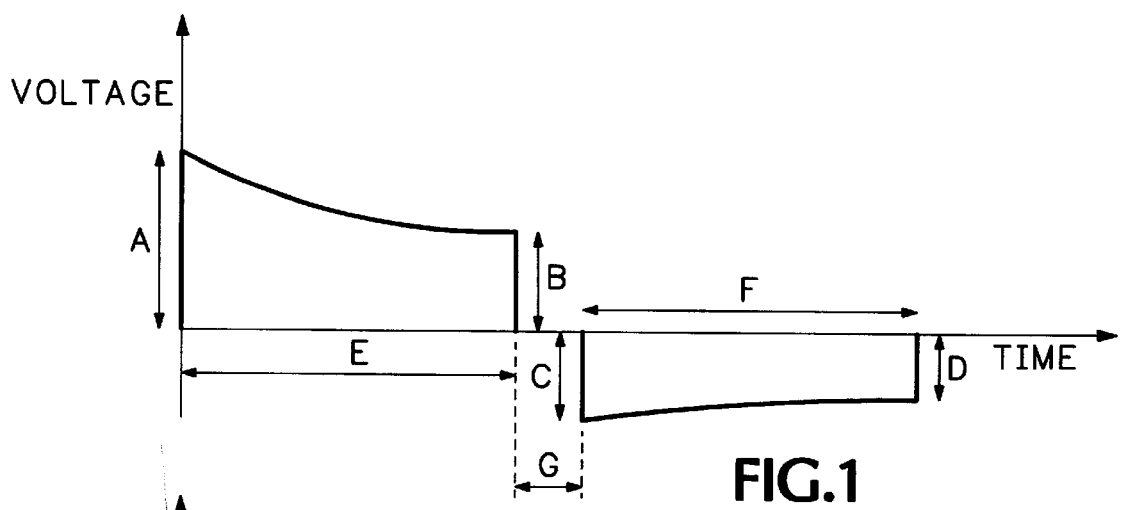
FIG. 1 shows a truncated exponential discharge waveform that would typically be associated with a patient having a relatively high impedance.
Figure 2:
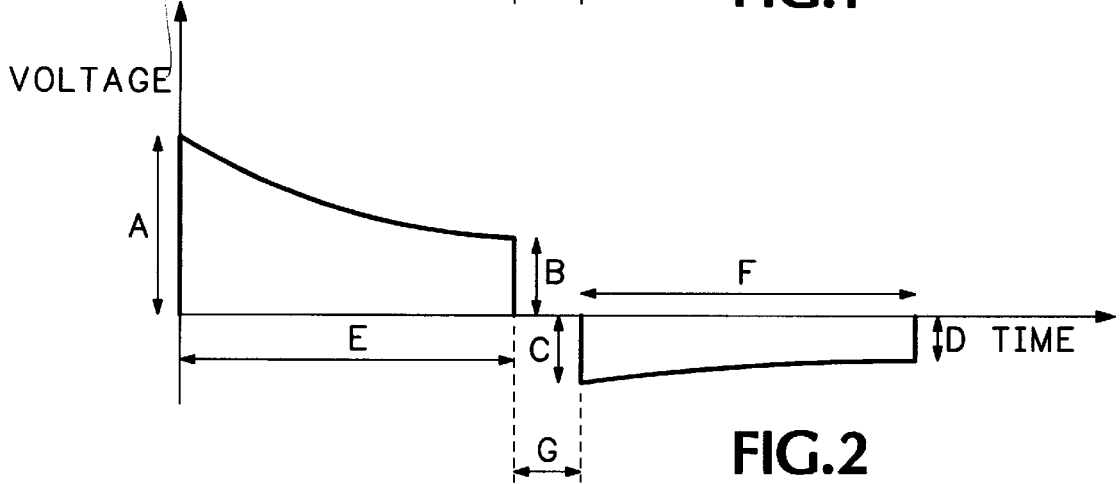
FIG. 2 shows a truncated exponential discharge waveform that would typically be associated with a patient having a relatively low impedance.

FIG. 1 and FIG. 2 illustrate the patient-to-patient differences that an external electrotherapy apparatus design must take into account. These figures are schematic representations of truncated exponential bi-phasic waveforms delivered to two different patients from an external electrotherapy apparatus. In these drawings, the vertical axis is voltage, and the horizontal axis is time. The principles discussed here are applicable to waveforms described in terms of current versus time as well. Furthermore, the principles discussed here are applicable to other types of waveforms which may be applied to a patient as part of electrotherapy such as damped sinusoid pulses or monophasic pulses.

The waveform shown in FIG. 1 is called a low-tilt waveform, and the waveform shown in FIG. 2 is called a high-tilt waveform, where tilt, H, is defined as a percent as follows:

$$H=((|A|-|D|)\div|A|)\times 100$$

As shown in FIGS. 1 and 2, A is the initial first phase voltage and D is the second phase terminal voltage. The first phase terminal voltage B results from the exponential decay over time of the initial voltage A through the patient, and the second phase terminal voltage D results from the exponential decay of the second phase initial voltage C in the same manner. The starting voltages and first and second phase durations of the FIG. 1 and FIG. 2 waveforms are the same. The differences in end voltages B and D reflect differences in patient impedance.

The electrotherapy apparatus operating voltages and energy delivery requirements affect the size, cost, weight and availability of components. In particular, operating voltage requirements affect the choice of switch and capacitor technologies. Total energy delivery requirements affect electrotherapy apparatus battery and capacitor choices. For a given patient, externally applied truncated exponential bi-phasic waveforms defibrillate at lower voltages and at lower total delivered energies than externally applied monophasic waveforms. In addition, there is a complex relationship between total pulse duration, first to second phase duration ratio, initial voltage, total energy and total tilt.

Up to a point, the more energy delivered to a patient in an electrotherapeutic pulse, the more likely the defibrillation attempt will succeed. Low-tilt bi-phasic waveforms achieve effective defibrillation rates with lower peak current than high-tilt waveforms. On the other hand, electrotherapy apparatus's delivering high-tilt bi-phasic waveforms deliver higher peak current to the patient than electrotherapy apparatus's delivering low-tilt waveforms while maintaining high efficacy up to a certain critical tilt value. Thus, for a given capacitance value, a given initial voltage and fixed phase durations, high impedance patients receive a waveform with less total energy and lower peak currents but better conversion properties per unit of energy delivered, and low impedance patients receive a waveform with more delivered energy and higher peak currents. By including in the electrotherapy apparatus the capability to dynamically adjust the waveform in response to measurements related to patient impedance, the difference in energy delivered to high impedance patients and low impedance patients is reduced.

The ideal result of the application of a defibrillation pulse to a patient is that the ventricular defibrillation is halted after the application of a single pulse, whether the delivered pulse is monophasic, bi-phasic, damped sinusoid, or of some other pulse shape. For high impedance patients, an insufficient peak amplitude of the current delivered to the heart on the first pulse may not halt fibrillation. For low impedance patients, a large peak amplitude of current may supply more energy to the heart than required for defibrillation. What is needed is a way to optimize the peak amplitude of the current delivered to the patient from the first pulse that can be adjusted according to the impedance of the patient. In addition, the shape of the applied pulse should be dynamically adjusted during application of the pulse to improve the effectiveness of the defibrillation attempt.

In order to optimally compensate for the impedance variations between patients prior to the first electrotherapy waveform, the electrotherapy apparatus would preferably have the capability to estimate the impedance of the patient without the application of high voltages. This could be accomplished by the application of a low level voltage or low level current signal to the electrodes while measuring the corresponding resulting current or voltage which results. Because the voltage which results from an applied current is proportional to the impedance, and because the current which results from an applied voltage is inversely proportional to the impedance, the measurements may be used directly as an indication of the impedance.

Using a measured parameter related to the patient impedance, patients could be classified into a plurality of predetermined ranges, such as ranges for patients having impedances greater than 100 ohms, impedances greater than 60 ohms and less than or equal to 100 ohms, and impedances less than or equal to 60 ohms. The initial voltage level applied to the patient during the first pulse would be one of a first set of values based upon the range into which the patient was placed using the impedance estimation. For example, patients having an estimated impedance of greater than 100 ohms would have an initial applied voltage of 1790 volts. Patients having an estimated impedance of greater than 60 ohms and less than or equal to 100 ohms would have an initial applied voltage of 1500 volts. Patients having an estimated impedance of less than or equal to 60 ohms would have an initial applied voltage of 1200 volts.

Other schemes for varying the initial applied voltage are possible. For example, the low level estimate of the impedance could be used to interpolate between a predetermined range of possible initial voltages. This would provide a nearly continuous spread of possible voltages between the extremes of the range of possible initial voltages. It should be recognized that similar control could be applied to the application of a current pulse to the patient. In this case, the impedance estimate would be used to set the initial applied current. As was the case for the application of a voltage pulse, the amplitude of the initial applied current could be determined by classifying the impedance estimate into three ranges and setting the initial applied current according to which of the impedance ranges the impedance estimate belongs. Alternatively, interpolation could be used to set the initial current level in a manner similar to setting the interpolation level for the initial voltage level.

Figure 3:
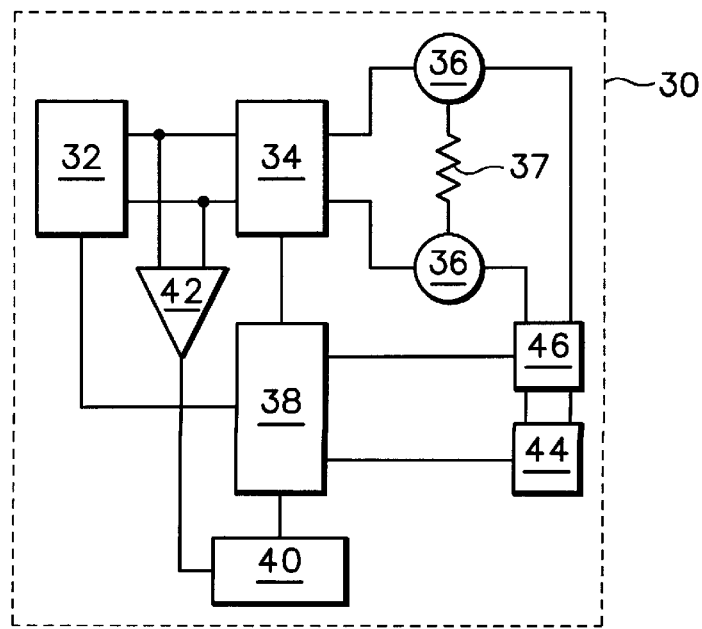
FIG. 3 shows a high level block diagram of a first electrotherapy apparatus.

Shown in FIG. 3 is a high level block diagram of a first electrotherapy apparatus 30, such as a defibrillator, which can perform the impedance measurement as well as the dynamic impedance compensation. The first electrotherapy apparatus 30 includes an energy source 32 to provide current pulses or the voltage pulses of the type shown in FIG. 1 and FIG. 2. Energy source 32 may include, for example, a single capacitor or a capacitor bank arranged to act as a single capacitor. A first connecting mechanism 34 selectively connects and disconnects energy source 32 to and from a pair of electrodes 36 electrically attached to a patient, represented here as a resistive load 37. The connections between the electrodes 36 and the energy source may be in either of two polarities with respect to positive and negative terminals on the energy source 32. The first electrotherapy apparatus is controlled by a controller 38. Specifically, controller 38 operates the first connecting mechanism 34 to connect energy source 32 with electrodes 36 in one of the two polarities or to disconnect energy source 32 from electrodes 36. Additionally, controller 38 is coupled to energy source 32 to control the initial energy delivered by energy source 32. A sensor 42 monitors a parameter associated with energy source 32 indicating the energy delivered by energy source 32 to the patient. Controller 38 receives timing information from a timer 40, and timer 40 receives electrical information from sensor 42 connected across energy source 32. Alternatively, the function of timer 40, or a related capability, may be incorporated into controller 38 with sensor 42 directly coupled to controller 38. Sensor 42 may be a voltage sensor, a current sensor, or a charge sensor, depending upon the way in which the waveform supplied by energy source 32 will be controlled. A measuring device 44, for measuring a parameter related to the patient impedance, is coupled to second connecting mechanism 46. Second connecting mechanism 46 is also coupled to electrodes 36. A control line from controller 38 is coupled to second connecting mechanism 46 to control the connection of measuring device 44 to electrodes 36. The parameter measured by measuring device 44 serves as an estimate for the impedance presented by load 37 (representative of the patient impedance) to energy source 32 when it is connected to load 37 by first connecting mechanism 34. The output of the measuring device 44 is coupled to controller 38.

Figure 4:
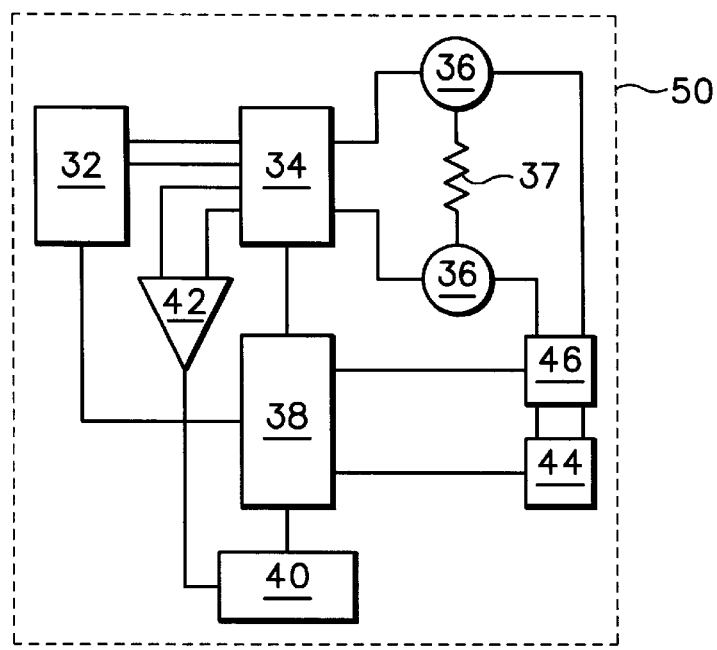
FIG. 4 shows a high level block diagram of a second electrotherapy apparatus.

Shown in FIG. 4 is a high level block diagram of a second electrotherapy apparatus 50, such as a defibrillator, which can perform the impedance measurement as well as the dynamic impedance compensation. In second electrotherapy apparatus 50, sensor 42 is coupled to first connecting mechanism 34 to measure a parameter related to the energy delivered to resistive load 37. The output of sensor 42 is coupled to timer 40. Timer 40 provides timing information to controller 38 used to control the actuation of first connecting mechanism 34. Alternatively, the function of timer 40, or a related capability, may be incorporated into controller 38 with sensor 42 directly coupled to controller 38. Controller 38 actuates second connecting mechanism 46 to couple measuring device 44 to electrodes 36 in order to perform a low level impedance measurement of resistive load 37.

First electrotherapy apparatus 30 and second electrotherapy apparatus 50 each include second connecting mechanism 46 to disconnect measuring device 44 from electrodes 36 during application of an electrotherapy waveform to resistive load 37. Disconnection protects measuring device 44 from the high voltages present on electrodes 36 during application of the electrotherapy waveform. It is possible to design a measuring circuit capable of withstanding the application of these high voltages. If such a measuring circuit were used in first electrotherapy apparatus 30 and second electrotherapy apparatus 50, second connecting mechanism 46 would not be necessary.

Figure 5:
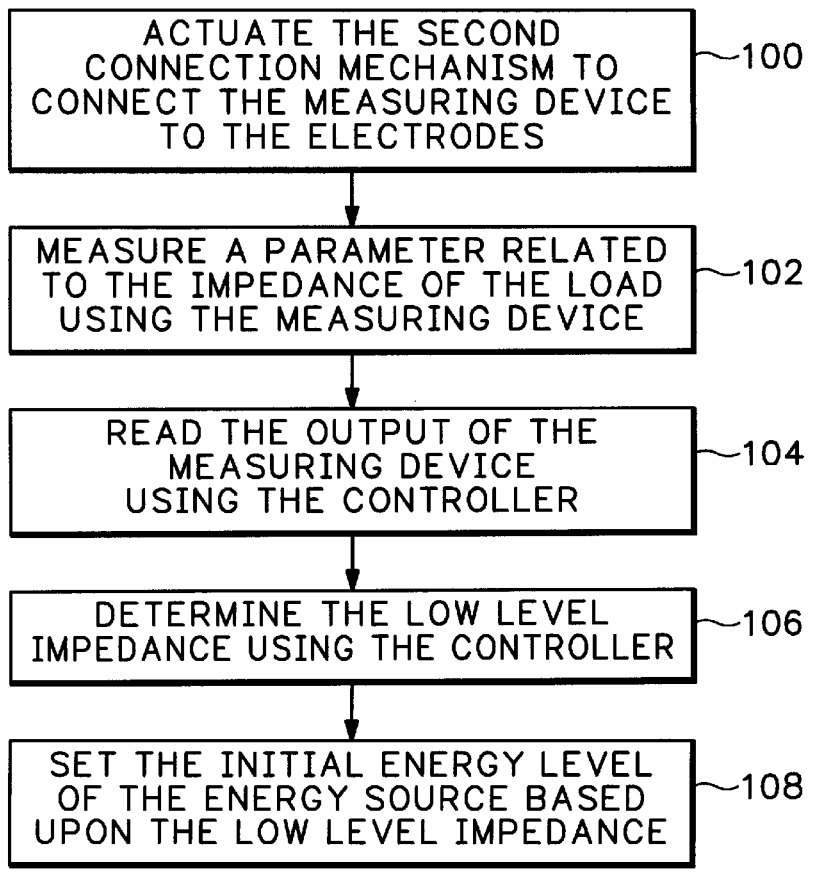
FIG. 5 shows a high level flow diagram of a method for setting the initial level of energy for the electrotherapy waveform to be applied to the patient using either the first electrotherapy apparatus shown FIG. 3 or the second electrotherapy apparatus shown in FIG. 4.

Shown in FIG. 5 is a high level flow diagram of a method of using the hardware shown in FIG. 3 or FIG. 4 to configure energy source 32 by setting its energy level. First, in step 100, controller 38 actuates second connection mechanism 46 to connect measuring device 44 to electrodes 36. Next, in step 102, measuring device 44 measures a parameter related to the impedance of load 37. Then, in step 104, controller 38 reads the output of measuring device 44. Next, in step 106, controller 38 determines the low level impedance. Finally, in step 108, based upon the low level impedance measurement, controller 38 sets the energy level of energy source 32 in preparation for performing electrotherapy. During the application of the electrotherapy waveform, first electrotherapy apparatus 30 or second electrotherapy apparatus 50 dynamically adjusts the electrotherapy waveform applied to the patient in response to a parameter related to patient impedance.

For the case in which the energy source includes a capacitor or a bank of capacitors, controller 38 controls the initial voltage to which the capacitors are charged. Controller 38 could use a predefined set of initial charge voltages based upon the impedance estimates obtained from measuring device 44. Alternatively, controller 38 could use the impedance estimate obtained from measuring device 44 to generate an initial charge voltage through interpolation.

A substantial benefit results from performing a low level measurement of the patient impedance prior to application of the electrotherapy waveform. An objective of using dynamic waveform control is to adjust the characteristics of the electrotherapy waveform based upon the patient impedance. However, the dynamic adjustment of the applied waveform occurs after application of the electrotherapy waveform. Therefore, the magnitude of the current that flows at the beginning of the application of the electrotherapy waveform may vary substantially depending upon the patient impedance. By combining a low level impedance measurement to set the energy level of energy source 32 with dynamic waveform control, additional compensation for impedance variations between patients is achieved. Setting the energy level of energy source 32 (which may, for example, be the voltage stored on a capacitor) based upon the low level impedance measurement reduces the range over which the magnitude of the peak current will vary as the patient impedance changes. Improving the match between the patient impedance and the applied electrotherapy waveform improves the efficacy of the electrotherapy. If the energy level of the energy source was set after applying an electrotherapy waveform having a nominal energy level, the benefit of reducing the range over which the peak current varies would not be achieved during application of that electrotherapy waveform.

Low level impedance measurement with dynamic waveform control could be used to optimize escalating energy protocols (electrotherapy methods that increase the energy on successive defibrillation attempts). Performing a low level impedance measurement to set the energy level of the energy source 32 prior to the application of the first electrotherapy waveform would allow the electrotherapy waveform applied to the patient to more closely match the patient impedance beginning with the first applied electrotherapy waveform. By setting the energy level of energy source 32 based upon the measured patient impedance, there is the possibility of achieving defibrillation with less energy than would be used if the energy level of energy source 32 were set based upon an average patient impedance. This is accomplished while ensuring that high impedance patients will receive therapeutically beneficial levels of energy.

Figure 6A:
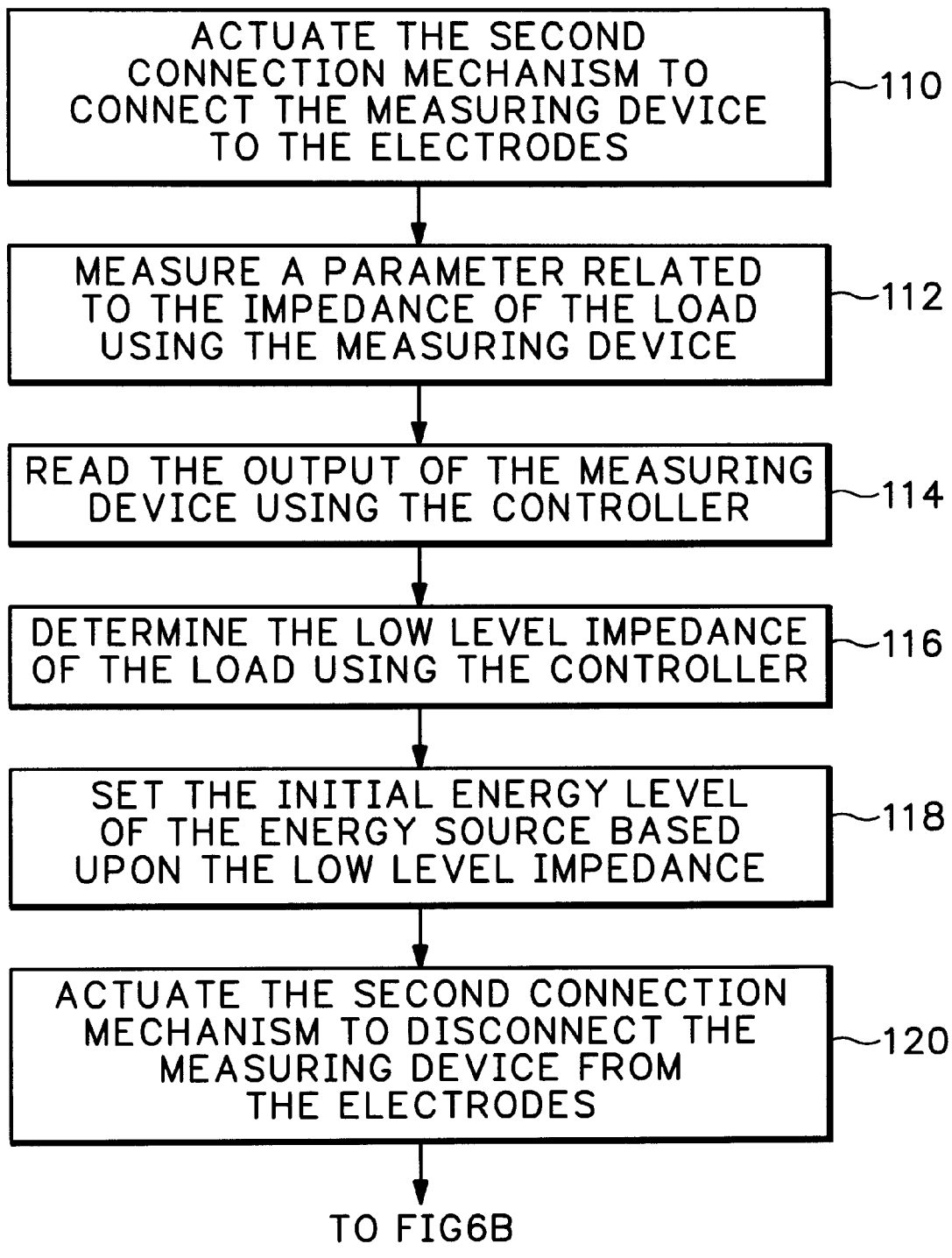
FIGS. 6A and 6B show a high level flow diagram of a method for using either the first electrotherapy apparatus shown FIG. 3 or the second electrotherapy apparatus shown in FIG. 4 to calibrate the low level impedance measurement.
Figure 6B:
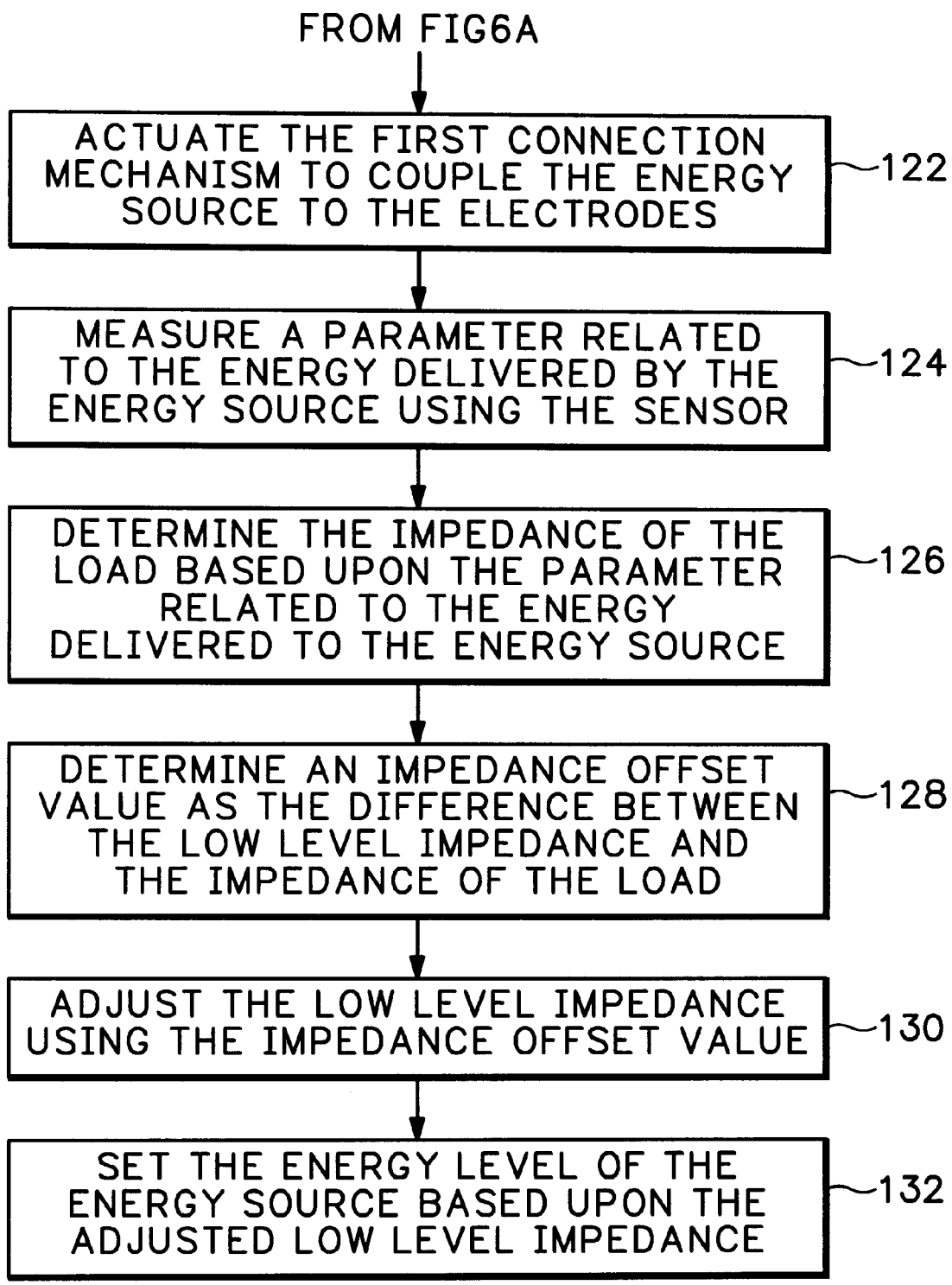

Alternative embodiments of the first electrotherapy apparatus 30 shown in FIG. 3 and second electrotherapy apparatus 50 shown in FIG. 4 include the capability to calibrate the accuracy of the low level impedance measurement made prior to application of each electrotherapy waveform. Shown in FIGS. 6A and 6B is a high level flow diagram of a method for using the alternative embodiments of first electrotherapy apparatus 30 or second electrotherapy apparatus 50 to set the energy level of energy source 32 and perform electrotherapy. In a first step 110, controller 38 actuates second connection mechanism 46 to connect measuring device 44 to electrodes 36. Next, in step 112, measuring device 44 measures a parameter related to the impedance of load 37. Then in step 114, controller 38 reads the output of measuring device 44. Next, in step 116, controller 38 determines the low level impedance of resistive load 37. Then, in step 118, based upon the impedance estimate, controller 38 sets the initial energy level of energy source 32 in preparation for performing electrotherapy. Next, in step 120, controller 38 actuates second connection mechanism 46 to disconnect measuring device 44 from electrodes 36. Then, in step 122, controller 38 actuates first connecting mechanism 34 to couple energy source 32 to electrodes 36. Next, in step 124, sensor 42 measures a parameter related to the energy delivered by energy source 32. Then, in step 126, controller 38 determines the impedance of resistive load 37 (representing the patient) using the parameter related to the energy delivered by energy source 32 and the energy level setting of energy source 32 prior to application of the electrotherapy waveform. In step 128, controller 38 determines an impedance offset value as the difference between the low level impedance determined in step 116 and the impedance determined in step 126. Next, in step 130, controller 38 adjusts the low level impedance using the impedance offset value. Finally, in step 132, controller 38 sets the energy level of energy source 32 based upon the adjusted low level impedance after decoupling energy source 32 from electrodes 36.

The adjustment of the low level impedance measurement by the impedance offset value can be regarded as a calibration of the low level impedance measurement. The impedance offset value is used for the next application of an electrotherapy waveform in order adjust the low level impedance measurement made prior to application of the electrotherapy waveform. The energy level of energy source 32 is then set based upon the low level impedance measurement adjusted by the impedance offset value. In this manner the energy level of energy source 32 is more closely adjusted to match patient impedance than would be the case if the energy level of energy source 32 were set based upon the low level impedance measurement without adjustment. The impedance offset value can itself be updated after the application of each electrotherapy waveform by determining the difference between the most recent low level impedance measurement and the impedance measurement made after the application of the electrotherapy waveform.

The variability between low level impedance measurements performed over a period of time provides an indication of the reliability of the low level impedance measurement. A relatively large variation in the low level impedance measurement (in the range of at least 10% to 20%) indicates the likelihood of problems in the coupling of the electrotherapy apparatus to the patient. The problems that can give rise to low level impedance measurement variations include contact problems between the electrodes and the patient or defects in the electrodes. The low level impedance variations may be detected before application of the first electrotherapy waveform or between the application of electrotherapy waveforms.

The controller in the electrotherapy apparatus could be configured to inform the user when relatively large low level impedance variations have been detected, provide an opportunity to the user to complete suggested corrective action, and then perform multiple low level impedance measurements to determine if the problem has been corrected. Alternatively, the electrotherapy apparatus could proceed with the application of electrotherapy using a previously selected energy level or a default energy level when relatively large variations in the low level impedance measurement are detected. In yet another alternative, the electrotherapy apparatus could prompt the user to correct the problem and, if the user is unsuccessful, apply electrotherapy using a previously selected energy level or a default energy level.

The use of a low level impedance measurement to set the energy level of energy source 32 has an advantage over measurement of the patient impedance based primarily upon parameters measured from application of an electrotherapy waveform to set the energy level of an energy source. Using a low level impedance measurement allows the energy level of the energy source to be set prior to application of the first electrotherapy waveform, thereby more closely matching the applied energy to the patient impedance. Those methods that adjust the energy level based upon patient impedance by first applying an electrotherapy waveform corresponding to a level of energy optimized for a patient having nominal impedance may provide more energy than necessary for low impedance patients and less than the optimal amount of energy for high impedance patients.

The use of low level impedance measurement to set the energy level of energy source 32 also has an advantage over electrotherapy methods that vary resistance in series with the patient in order to control the current waveform applied to the patient. These methods generally set the energy level of the energy source so that sufficient energy is available for high impedance patients. The resistance in series with the patients is set to correspond to a nominal patient impedance. After application of the electrotherapy waveform, the impedance in series with the patient is adjusted to set the current at the desired level. Using series resistance is a relatively inefficient way of controlling the current delivered to the patient. For example, if the energy level of the energy source is set sufficiently high to deliver optimal energy to a patient having 150 ohms of impedance (a high impedance patient), and electrotherapy is actually performed on a patient having 75 ohms of impedance (a patient of nominal impedance), then (assuming the series resistance was initially set for a patient having nominal impedance) approximately half of the energy of the energy source will be dissipated in the series resistance. In contrast, using a small signal impedance measurement to set the energy level of energy source 32, results in the application of more therapeutically optimal levels of energy for patient impedances ranging from low to high without the wasteful dissipation of energy in series resistors. This performance is particularly important because of the limited energy available for electrotherapy in portable electrotherapy apparatuses.

Figure 7:
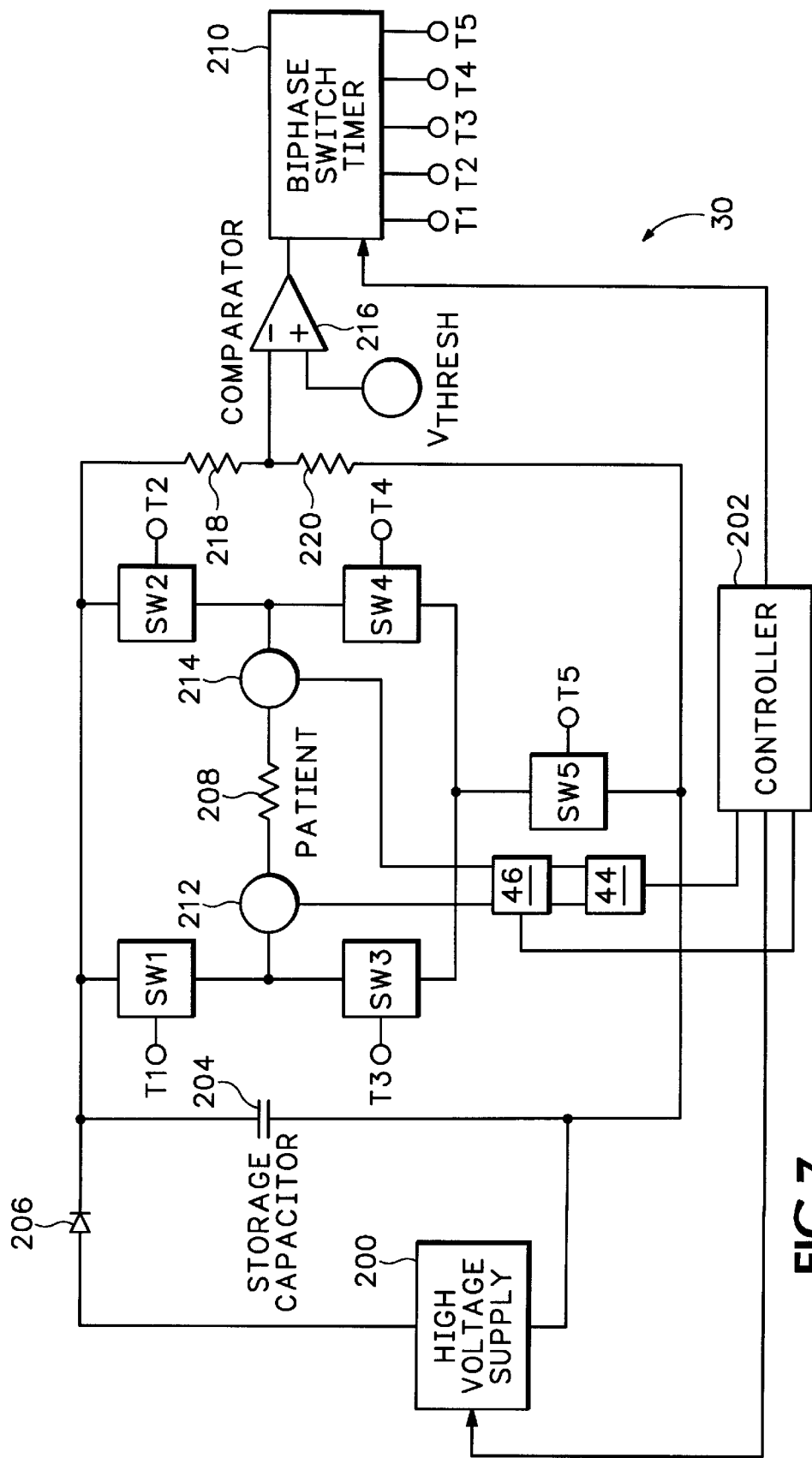
FIG. 7 shows a first embodiment of the first electrotherapy apparatus shown in FIG. 3.

Shown in FIG. 7 is a simplified schematic showing a first embodiment of the first electrotherapy apparatus 30 represented by the block diagram shown in FIG. 3. High voltage power supply 200 is configured by controller 202 to charge storage capacitor 204 through blocking diode 206. The target charge level of storage capacitor 204 is set by controller 202 based upon of the low level measurement of patient impedance 208. The low level estimation of patient impedance 208 is performed using measuring device 44. Controller 202 receives the output from measuring device 44 to obtain an estimate of patient impedance 208. Using this estimate of patient impedance 208, controller 202 charges storage capacitor 204 to an initial voltage corresponding to patient impedance 208. The initial charge voltage value is selected, based upon the impedance estimate, so that the peak current delivered to the patient at the start of the discharge is sufficiently large for defibrillation but not substantially beyond the level needed for defibrillation.

During the charging of storage capacitor 204 by high voltage power supply 200, switches SW1, SW2, SW3, and SW4 are open so that no voltage is applied to patient impedance 208. During the charging of storage capacitor 204, switch SW5 is closed. After storage capacitor 204 has been charged to its target voltage by high voltage power supply 200, controller 202 stops high voltage power supply 200 from further charging storage capacitor 204.

Bi-phasic switch timer 210 controls switches SW1, SW2, SW3, SW4, and SW5 by using the respective control signals T1, T2, T3, T4, and T5. In response to a signal from controller 202, bi-phasic switch timer 210 initiates the discharge of storage capacitor 204 through first electrode 212 and second electrode 214. Bi-phasic switch timer 210 initiates the discharge of storage capacitor 204 for the first phase of the bi-phasic pulse by closing switch SW1 and switch SW4. With switch SW5 previously closed by bi-phasic switch timer 210, closing switch SW1 and switch SW4 applies the voltage stored on storage capacitor 204 across patient impedance 208. Depending on the electrotherapy method in use, the delivery of the first phase voltage may be terminated by bi-phasic switch timer 210 after the expiration of a predetermined time period or when the voltage across storage capacitor 204 has dropped to a predetermined value. Termination of the delivery of the first phase of the bi-phasic pulse is done by opening switch SW5 using control signal T5 and then opening switch SW1 and switch SW4 using, respectively, control signals T1, and T4.

Controller 202 delays for the time period G shown in FIG. 10 and FIG. 11 before initiating the second phase of the bi-phasic pulse. In preparation for the second phase, switch SW5 is closed. At the end of time period G between the first and the second phases, bi-phasic switch timer 210 closes switch SW2 and switch SW3 using, respectively, control signals T2 and T3. By closing switch SW2 and switch SW3, the polarity of the voltage applied during the second phase is opposite the polarity of the voltage applied in the first phase. The second phase is terminated when bi-phasic switch timer 210 opens switch SW5. The termination of the second phase may occur at the end of a predetermined period of time or when the voltage across storage capacitor 204 has dropped to a predetermined value.

Comparator 216 compares the voltage across storage capacitor 204 to a threshold value in order to determine when the voltage across storage capacitor 204 reaches the threshold value. The resistor divider formed by first resistor 218 and second resistor 220 scales the voltage applied to comparator 216. Depending upon the electrotherapy method applied, termination of the first phase may be done after a predetermined time or when the voltage across storage capacitor 204 reaches the threshold value. Termination of the second phase of the bi-phasic pulse is done after a predetermined time period.

A variety of components may be used to implement switches SW1–SW5. For the schematic shown in FIG. 7, an insulated gate bipolar transistor (IGBT) could be used for switch SW5 and silicon controlled rectifiers could be used for switches SW1–SW4. An IGBT acts as a voltage controlled electronic switch. For voltages applied to the base that are greater than a threshold value, current can flow between the collector and the emitter. The IGBT is turned off by removal of the base voltage. In contrast to this, a silicon controlled rectifier (SCR) is an avalanche switch which enters a conductive state by the application of a trigger signal to a control terminal. Until the current through the SCR approaches zero, the SCR will remain in the conductive state. For switches SW1 and SW4 or switches SW2 and SW3 to conduct with the application of a trigger signal, switch SW5 must be closed. In the schematic shown in FIG. 7, switch SW5 is opened to interrupt the flow of current through, either switch SW1 and switch SW4 or switch SW2 and SW3 at the end of either the first phase or the second phase.

By placing switch SW5 as it is in the schematic shown in FIG. 7, switch SW5 does not have to withstand the maximum voltage stored across storage capacitor 204. When all of switches SW1 through SW5 are open. The voltage that switch SW5 must withstand is divided across the SCR's and the IGBT. When switch SW5 is opened by bi-phasic timer switch 210, the voltage applied across switch SW5 is very nearly the entire capacitor voltage. However, at this time, the voltage across storage capacitor 204 has decayed substantially. Other configurations of storage capacitors and switches may be used to deliver a bi-phasic pulse to the patient. In addition, the circuit disclosed in FIG. 7 could be used to deliver a variety of pulses other than bi-phasic.

Figure 8:
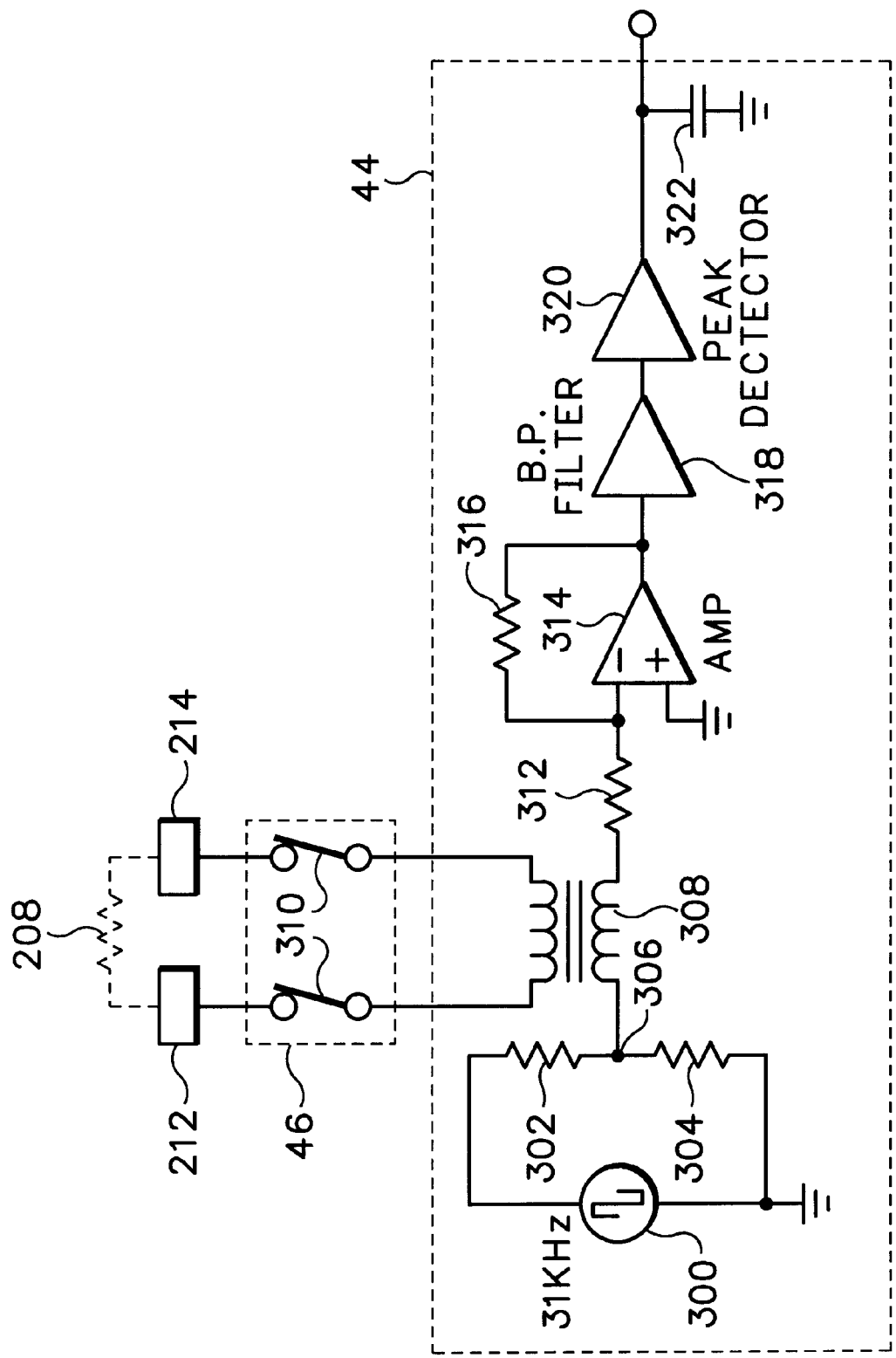
FIG. 8 shows a measuring device that could be used with any of the embodiments of the first electrotherapy apparatus or the second electrotherapy apparatus.

An embodiment of the measuring device 44 is included in the simplified schematic shown in FIG. 8. In this embodiment of measuring device 44, the parameter related to patient impedance is a voltage at the output of a filter. It should be recognized that other parameters, such as current, could be used to estimate the patient impedance. A signal source 300 supplies a square wave having a frequency of approximately 31 Khz and an amplitude of 5 volts peak to peak. A voltage divider formed of resistor 302 and resistor 304 attenuates the square wave provided by signal source 300 so that a peak to peak voltage of about 25 millivolts is present at circuit node 306. It should be recognized that other signal source frequencies and amplitudes could be used for measuring the parameter related to patient impedance. Furthermore, other values of resistor 302 and resistor 304 could be used to divide the voltage supplied by signal source 300.

Node 306 is connected to the primary side of isolation transformer 308. The secondary side of isolation transformer 308 is connected through single throw double pole relay 310 to first electrode 212 and second electrode 214. Isolation transformer 308 reflects the patient impedance 208 from its secondary side to its primary side. Therefore, the current flow through the primary side of isolation transformer 308 is affected by patient impedance 208. The current flowing through the primary side of isolation transformer 308 flows through resistor 312 and into the virtual ground at the inverting input of amplifier 314. Resistor 316, connected from the inverting input to the output of amplifier 314, resistor 312, and amplifier 314 form an inverting amplifier having a gain approximately equal to the ratio of the values of resistor 316 and resistor 312.

The output of amplifier 314 is coupled to the input of bandpass filter 318. The center frequency of bandpass filter 318 is tuned to the frequency of signal source 300. The output of bandpass filter 318 is a sine wave having the fundamental frequency of signal source 300. The amplitude of the sine wave output of bandpass filter 318 is a function of the magnitude of patient impedance 208.

The output of bandpass filter 318 is coupled to the input of peak detector 320. Peak detector 320. Peak detector 320 stores the peak value of the sine wave output from bandpass filter 318 onto capacitor 322. Peak detector may be implemented using an operational amplifier configured as a voltage follower with the output of the voltage follower connected to the anode of a schottky diode. The cathode of the schottky diode would be coupled to capacitor 322. Controller 202 includes an A/D converter to convert the voltage on capacitor 322 to a digital value and compute a low level value for patient impedance 208 from this digital value.

Figure 9:
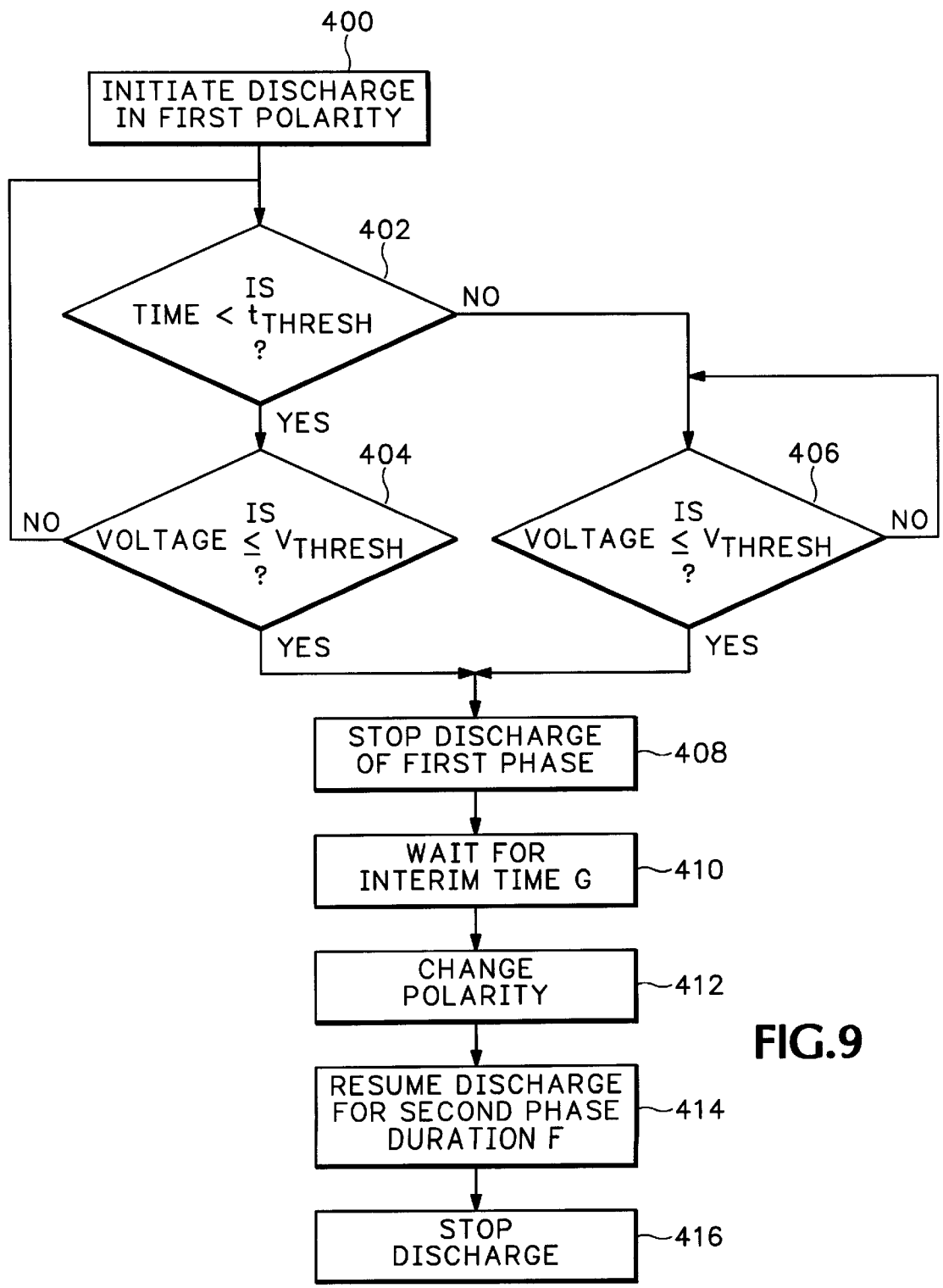
FIG. 9 shows a high level flow diagram of a method of using the first embodiment of the first electrotherapy apparatus shown in FIG. 7 to dynamically adjust the waveform applied to the patient.

Shown in FIG. 9 is a high level flow diagram of a method of using the hardware shown in FIG. 3 to dynamically adjust the waveform applied by energy source 32 to load 37 in response to real time measurements of waveform parameters. The method shown in FIG. 9 corresponds to the case in which energy source 32 is formed from a capacitor or a bank of capacitors. The first step of the method shown in FIG. 9 would follow the measurement of the parameter related to the impedance of load 37 shown in FIG. 3.

In step 400, controller 38 actuates connecting mechanism 34 to initiate the flow of energy from energy source 32 into load 37. Then, in step 402, controller 38 determines if the time elapsed since the initiation of the flow of energy from energy source 32 into load 37 is less than a predetermined threshold value of time. The predetermined threshold value of time is selected based upon the empirically determined minimum period of time required for delivery of an effective first phase of the electrotherapy waveform. If the time elapsed is less than the threshold value of time, then, in step 404, controller 38 determines if the voltage provided by energy source 32 is less than or equal to a threshold value of voltage. The predetermined threshold value of voltage is selected based upon the empirically determined minimum delivered energy required for delivery of an effective first phase of the electrotherapy waveform. If the voltage provided by energy source 32 is not less than or equal to the threshold value of voltage, then controller 38 returns to step 402 in which it determines if the elapsed time is less than the predetermined threshold value of time.

If controller 38 determines that the elapsed time is greater than the predetermined threshold value of time, then, in step 406, controller 38 determines if the voltage provided by energy source 32 is less than or equal to the predetermined threshold value of voltage. If the voltage is not less than the predetermined threshold value of voltage, then controller 38 continues to determine if the voltage provided by energy source 32 is less than or equal to the predetermined threshold value of voltage.

If either of the steps of determining if the voltage provided by energy source 32 is less than or equal to the predetermined threshold value of voltage determines that this is the case, then, in step 408, controller 38 stops the discharge of energy source 32 to terminate the first phase of the bi-phasic pulse. Next, in step 410, controller 38 waits for the predetermined time interval G between the first and second phases of the bi-phasic pulse. Then, in step 412, connecting mechanism 34 switches the polarity of the applied voltage by energy source 32 to load 37. Next, in step 414, controller 38 initiates the discharge of the second phase of the bi-phasic pulse for a predetermined time interval F. Finally, at the end of the predetermined time interval F, in step 416, controller 38 stops the discharge of energy source 32 by disconnecting energy source 32 from electrodes 36 using connecting mechanism 34. Additional detail regarding the first embodiment of the first electrotherapy apparatus can be found in U.S. Pat. No. 5,593,427 issued to Gliner et al. and incorporated by reference into this specification.

For patients having a high impedance, the method shown in FIG. 9 produces the type of waveform shown in FIG. 10. For the waveform in FIG. 10, the time period E of the first phase of the bi-phasic pulse is extended past the predetermined threshold value of time so that energy source 32 discharges to the predetermined threshold value of voltage before the first phase is terminated. For patients having a low impedance, the method shown in FIG. 9 produces the type of waveform shown in FIG. 11. For the waveform in FIG. 11, the first phase of the bi-phasic pulse is terminated before the predetermined threshold value of time is reached when the predetermined threshold value of voltage is reached during the discharge of energy source 32. Therefore, the method shown in FIG. 9 dynamically adjusts the waveform applied by energy source 32 to the patient in response to the patient impedance detected by controller 38.

Figure 12:
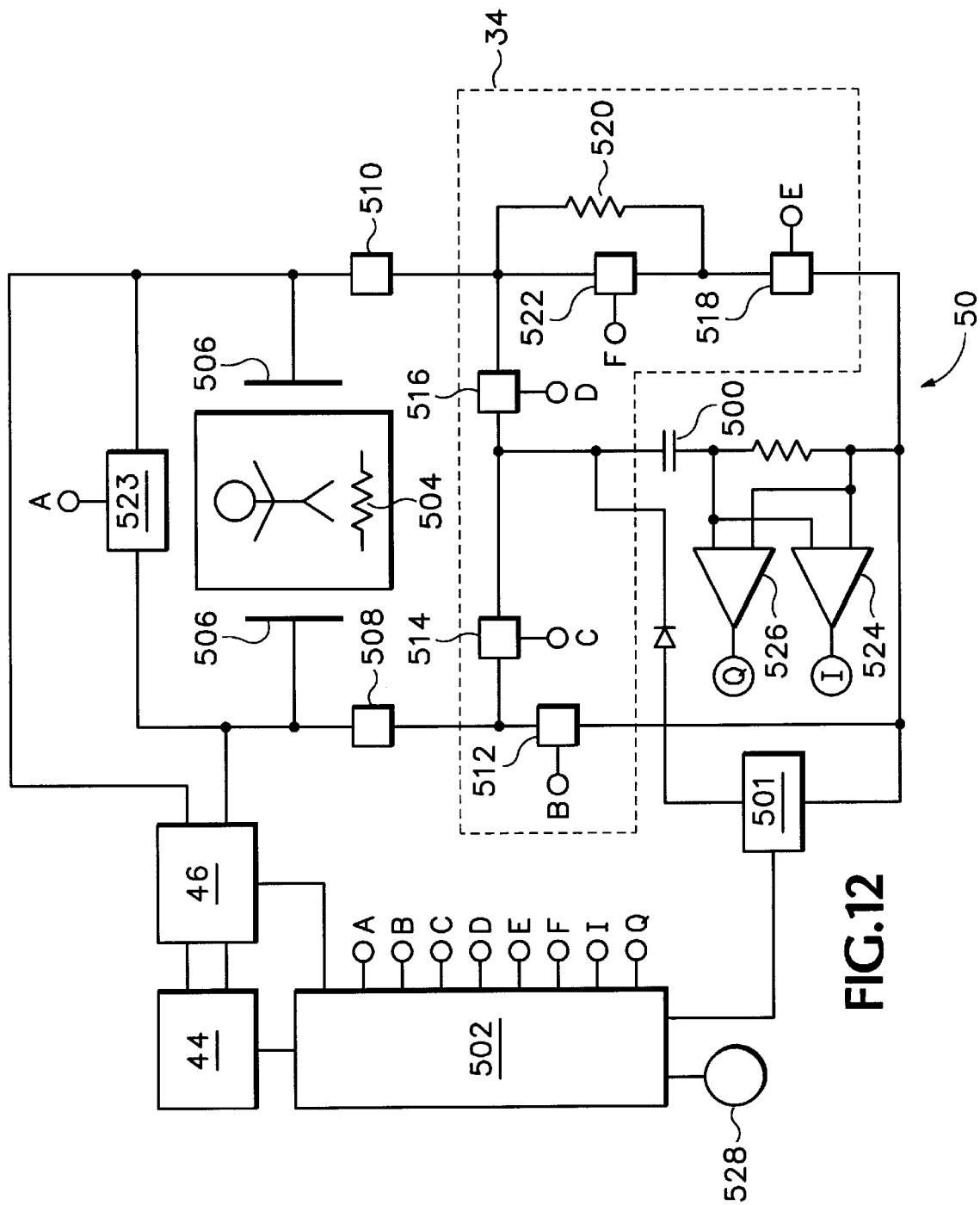
FIG. 12 shows a first embodiment of the second electrotherapy apparatus shown in FIG. 4.

Shown in FIG. 12 is a simplified schematic showing a first embodiment of the second electrotherapy apparatus 50 represented by the block diagram shown in FIG. 4. In FIG. 12, the energy source is a capacitor 500 having a capacitance value between 60 and 150 microfarads, with an optimal capacitance value of 100 microfarads. The first embodiment also includes a charging mechanism, such as high voltage power supply 501, for charging capacitor 500 to an initial voltage. An controller 502 controls the operation of the electrotherapy apparatus 50 to deliver an electrotherapy waveform to the patient impedance 504 through electrodes 506 automatically in response to a detected arrhythmia or manually in response to a human operator.

Switches 508 and 510 isolate the patient from the defibrillation circuitry until the application of bi-phasic pulse. Switches 508 and 510 may be any suitable kind of isolators, such as mechanical relays, solid state devices, spark gaps, or other gas discharge devices. In the first embodiment of the second electrotherapy apparatus 50, the first connecting mechanism 34 includes four switches 512, 514, 516, and 518 operated by the controller 502 to deliver an electrotherapy waveform from capacitor 500 to the patient.

The first embodiment of the second electrotherapy apparatus 50 may also include an optional current limiting circuit including a resistor 520 and switch 522 to provide additional protection to the circuit components and to the operator. In the description of the operation of the first embodiment of the second electrotherapy apparatus 50, all switches will be open prior to discharge of capacitor 500. However, it should be recognized that it is not necessary that all of the switches start out in the open position. For example, some of the switches could start out in the closed position, with the sequence of the switch openings modified accordingly.

Prior to the charging of capacitor 500 by high voltage power supply 501, measuring device 44 performs a low level measurement of patient impedance 504. Second connecting mechanism 46 connects measuring device 44 to electrodes 506 in order to perform the impedance estimate. When the impedance estimation is complete, controller 502 controls second connecting mechanism 46 to disconnect measuring device from electrodes 506. The measurement of the parameter related to the patient impedance serves as an estimate for the impedance presented by patient impedance 504 to capacitor 500. The output of the measuring device 44 is coupled to controller 502. Using this estimate of patient impedance 504, controller 502 controls high voltage power supply 501 to charge capacitor 500 to an initial voltage corresponding to patient impedance 504. The initial charge voltage value is selected, based upon the impedance estimate, so that the peak current delivered to the patient at the start of the discharge is sufficiently large for defibrillation but not substantially beyond the level needed for defibrillation.

In response to waveform analyzer 523 indicating a need for an electrotherapy waveform, controller 502 first closes switches 508 and 510, then switch 518, then switch 514 to initiate delivery of the electrotherapy waveform to the patient. A sensor 524 monitors the current delivered by capacitor 500. If the peak current is below a circuit safety threshold, then switch 522 is closed to take resistor 520 out of the circuit. Peak current values above the threshold could indicate a short circuit condition.

The duration of the first and second phases of the bi-phasic pulse are determined by measuring a patient-dependent electrical parameter. As described in more detail below, the measured parameter in the preferred embodiment is the time it takes for a predetermined amount of charge to be delivered by the energy source to the patient. Charge control can provide better noise immunity than other waveform monitoring methods, such as voltage or current monitoring. The first embodiment of the second electrotherapy apparatus 50 uses an integrator 526 to provide a measurement to the controller 502 of the charge delivered to the patient. The controller 502 sets the duration of the first and second phases (thereby controlling the waveform shape) based on charge measurements supplied by integrator 526. It should be recognized that other parameters may be monitored to control the length of the first and the second phases. For example, measurement of the voltage or current amplitude may be used to control the length of the first and second phases.

At the end of the first phase of the waveform, the controller opens switch 518 to terminate delivery of the electrotherapy waveform. Switch 522 may also be opened at any time onward from the time at which switch 518 is opened. The controller 502 opens switch 514 as well. After the lapse of a brief interphase period, the controller 502 closes switches 512 and 516 to initiate delivery of the second phase of the waveform. The second phase duration could be determined by the first phase duration. However, there are other ways in which the second phase duration may be determined. For example, the duration of the second phase could be set at a predetermined time. At the end of the second phase, the controller 502 opens switch 512 to terminate delivery of the electrotherapy waveform. Switches 516, 508, and 510 are opened after the opening of switch 512.

Following is a description of a specific implementation of the first embodiment of the second electrotherapy apparatus 50. In this example, switches 508 and 510 are implemented as a double pole, double throw mechanical relay. Switches 514 and 516 are each implemented as a pair of SCR's in series in order to meet the voltage blocking requirements with currently available components. Switch 518 is implemented as two insulated gate bipolar transistors ("IGBT's") in series, again to meet the voltage blocking requirements.

The functions of switches 522 and 518 are implemented using three series connected IGBT's to meet the voltage blocking requirements. The IGBT connected between the other two IGBT's is used by both switch 522 and switch 518. The middle IGBT is on at the same time as switch 522 is on and is off at the same time switch 518 is off. With the use of three IGBT's to implement the functions of switch 522 and 518, resistor 520 is split into two resistors to equally divide the voltage across two of the IGBT's.

The sensor 524 can be used to send current information to the controller 502 to detect shorting between electrodes 506 or the condition in which one or both of electrodes 506 are not connected to the patient. Sensor 524 and integrator 526 may each be implemented using an op-amp feeding a threshold comparator for detecting charge limits and current limits, respectively. The integrator 526 could include a switch for resetting to its initial conditions prior to the initiation of an electrotherapy waveform.

A comparator included in the integrator 526 monitors the charge delivered to the patient and sends a signal to the controller 502 when the charge reaches 0.06182 Coulombs (referred to as "Qt"). The time required to reach that charge ("t(Qt)") is monitored by the controller 502 using an up/down counter which counts a scaled down reference frequency. One element of the frequency scaler is a selectable 2:3 prescaler. Timer 528 includes the up/down counter, the 2:3 prescaler, and the frequency source for providing the timing information used by controller for controlling the discharge of capacitor 500. The pre-scaler is set to 3 during the first phase. In this example, eleven time thresholds are stored in the controller, which determines the first phase duration ("t($\phi$1)") based on the time required to reach Qt. At each time threshold, a new value of t($\phi$1) is loaded until Qt is reached. If Qt is not reached within 6.35 mS, then t($\phi$1) is set to 12 mS. The counter runs at the scaled down frequency during delivery of the entire first phase. Some exemplary values for Qt thresholds and t($\phi$1) are shown in Table I.

TABLE I

| If t(Qt) < (mS) | Then t($\phi$1) is (mS) |
|---|---|
| 1.13 | 2.3 |
| 1.60 | 2.85 |
| 2.07 | 3.79 |
| 2.56 | 4.02 |
| 3.07 | 4.83 |
| 3.58 | 6.76 |
| 4.10 | 7.73 |
| 4.64 | 8.69 |
| 5.20 | 9.66 |
| 5.77 | 10.62 |
| 6.35 | 11.59 |

In this example, the interphase delay is set at 300 $\mu$S. At 0 $\mu$S (the beginning of the delay between the first and the second phase) the first phase IGBT's are opened, terminating the first phase. At 250 $\mu$S, the second phase IGBT's are closed. At 300 $\mu$S the second phase SCR's are closed, initiating the second phase.

In this example, second phase timing is determined by first phase timing. Specifically, the count value accumulated during phase one (2.3 mS to 12 mS) is used to control the duration of the second phase. During the second phase, the counter that had been counted up during the first phase is counted down to 0, at which time the second phase is terminated. The actual duration of the second phase depends on the scaled down frequency used to run down the counter. If the first phase t(Qt) was less than 3.07 mS, then the reference clock prescaler is set to 3 to a give second phase duration equal to the first phase duration. If t(Qt) is greater than or equal to 3.07 mS, then the pre-scaler is set to 2, giving a second phase duration which is ⅔ of the first phase duration.

An alternative to the measurement of charge delivery to determine the length of the first phase of the bi-phasic pulse is the measurement of the voltage remaining on capacitor 500. In this implementation, a circuit, such as a voltage divider connected to a buffer amplifier, is used to monitor the voltage on capacitor 500. The output of the buffer amplifier is connected to a comparator. When the comparator detects a voltage level at the output of the buffer amplifier corresponding to a drop in the voltage on capacitor 500 to 1000 volts, a signal is sent to controller 502. Depending on the time (Vt) at which the voltage on capacitor 500 reaches 1000 volts, the duration of the first phase of the bi-phasic pulse is varied. As in the charge control embodiment, the time required to reach that voltage is monitored by the controller using an up/down counter which counts a scaled down reference frequency. The first phase duration (t($\phi$1)) is based on the time required to reach Vt. The method of selecting the appropriate t($\phi$1) is identical to the charge control embodiment. If Vt is not reached within 6.18 mS, then t($\phi$1) is set to 12 mS. Table II shows the t(Vt) thresholds and their associated lengths of the first phase, t($\phi$1). The interphase delay and determining the second phase timing are very similar to the charge control method.

TABLE II

| if t(Vt) < (mS) | Then t($\phi$1) is (mS) |
|---|---|
| 1.24 | 2.3 |
| 1.73 | 2.85 |
| 2.23 | 3.79 |
| 2.72 | 4.02 |
| 3.22 | 4.83 |
| 3.71 | 6.76 |
| 4.20 | 7.73 |
| 4.70 | 8.69 |
| 5.19 | 9.66 |
| 5.69 | 10.62 |
| 6.18 | 11.59 |

Although several embodiments of the invention have been illustrated, and their forms described, it is readily apparent to those of ordinary skill in the art that various modifications may be made therein without departing from the spirit of the invention or from the scope of the appended claims.

What is claimed is:

1. In an electrotherapy apparatus including an energy source, a method for applying electrotherapy to a patient, comprising:
    measuring a first parameter relating to an impedance of the patient;
    configuring the energy source based upon the first parameter;
    coupling the energy source to the patient;
    measuring a third parameter related to energy delivered to the patient by the energy source; and
    decoupling the energy source from the patient based upon the third parameter.

2. With the electrotherapy apparatus including a first connecting mechanism coupled between the energy source and a first electrode and a second electrode coupled to the patient, a measuring device configured for coupling to the first electrode and the second electrode, a controller coupled to the energy source, the first connecting mechanism, the measuring device, and a sensor, the method as recited in claim 1, wherein:
    measuring the first parameter includes using the measuring device;
    configuring the energy source includes setting a second parameter using the controller, with the second parameter based upon the first parameter and relating to the energy stored by the energy source;
    coupling the energy source to the patient includes actuating the first connecting mechanism using the controller to couple the energy source to the first electrode and the second electrode;

measuring the third parameter includes using the sensor; and decoupling the energy source from the patient includes actuating the first connecting mechanism using the controller to decouple the energy source from the first electrode and the second electrode based upon the third parameter.

3. The method as recited in claim 2, further comprising:

measuring the first parameter using the measuring device, with measuring the first parameter occurring after actuating the first connecting mechanism using the controller to decouple the energy source from the first electrode and the second electrode;

determining a first patient impedance based upon the third parameter; and setting the second parameter based upon the first parameter and the first patient impedance.

4. The method as recited in claim 3, wherein:

setting the second parameter based upon the first parameter and the first patient impedance includes determining a second patient impedance based upon the first parameter, determining a difference between the first patient impedance and the second patient impedance, and setting the second parameter based upon the difference and the second patient impedance.

5. The method as recited in claim 4, wherein:

measuring the first parameter using the measuring device includes applying a waveform having insufficient energy for electrotherapy to the patient through the first electrode and the second electrode.

6. The method as recited in claim 5, wherein:

setting the second parameter based upon the difference and the second patient impedance includes setting the second parameter based upon the sum of the second patient impedance and the difference.

7. The method as recited in claim 2, further comprising:

classifying the first parameter into one of a plurality of predetermined ranges with each of the predetermined ranges corresponding to one of a plurality of values, with setting the second parameter including setting the second parameter to the one of the values corresponding to the one of the predetermined ranges into which classifying the first parameter placed the first parameter, and with classifying the first parameter occurring after measuring the first parameter and before setting the second parameter.

8. The method as recited in claim 7, wherein:

the second parameter includes a voltage stored on a capacitor, with the capacitor included within the energy source.

9. The method as recited in claim 8, further comprising:

determining a first time interval based upon the third parameter, with determining the first time interval occurring after measuring the third parameter and occurring before actuating the first connecting mechanism to decouple the energy source from the first electrode and the second electrode.

10. The method as recited in claim 9, wherein:

the third parameter includes current flowing into the patient.

11. The method as recited in claim 9, wherein:

the third parameter includes a voltage on the capacitor.

12. The method as recited in claim 9, wherein:

the third parameter includes a charge delivered to the patient.

13. The method as recited in claim 12, wherein:

the first time interval includes a time required to deliver a predetermined amount of the charge to the patient, and;

actuating the first connecting mechanism to decouple the energy source from the first electrode and the second electrode includes determining a second time interval by classifying the first time interval into one of a plurality of predetermined time intervals, selecting one of a plurality of time values corresponding to the predetermined time intervals to set a length of time from the coupling of the energy source to the first electrode and the second electrode to the decoupling of the energy source from the first electrode and the second electrode.

14. The method as recited in claim 13, wherein:

the measuring device includes a second connecting mechanism for coupling and decoupling the measuring device to and from, respectively, the first electrode and the second electrode.

15. The method as recited in claim 14, wherein:

the first parameter includes a voltage.

16. An electrotherapy apparatus for performing electrotherapy on a patient through a first electrode and a second electrode, comprising:

an energy source to deliver energy to the patient through the first electrode and the second electrode;

a sensor configured to measure a first parameter related to the energy delivered to the patient;

a first connecting mechanism configured to couple and decouple the energy source to and from, respectively, the first electrode and the second electrode;

a measuring device configured to measure a second parameter that varies with patient impedance through the first electrode and the second electrode; and a controller coupled to the first connecting mechanism and the energy source, and arranged to receive the first parameter from the sensor, with the controller configured to actuate the first connecting mechanism to couple the energy source to the first electrode and the second electrode and configured to actuate the first connecting mechanism to decouple the energy source from the first electrode and the second electrode based upon the first parameter, and with the controller arranged to receive the second parameter from the measuring device to configure the energy source based upon the second parameter.

17. The electrotherapy apparatus as recited in claim 16, wherein:

the energy source includes a power supply and a capacitor, with the power supply for charging the capacitor.

18. The electrotherapy apparatus as recited in claim 17, wherein:

the second parameter includes an output voltage from the measuring device; and the measuring device includes a configuration for performing measurement of the second parameter through the first electrode and the second electrode.

19. The electrotherapy apparatus as recited in claim 18, wherein:

the controller includes a configuration to determine a first patient impedance based upon the first parameter, to determine a second patient impedance based upon the second parameter, to determine a difference between the first patient impedance and the second patient impedance, and to configure the energy source based upon the difference and the second patient impedance.

20. The electrotherapy apparatus as recited in claim 19, wherein:

the measuring device includes a configuration for performing measurement of the second parameter by applying a waveform having insufficient energy for electrotherapy to the patient through the first electrode and the second electrode.

21. The electrotherapy apparatus as recited in claim 20, wherein:

the controller includes a configuration to configure the energy source based upon the sum of the second patient impedance and the difference.

22. The electrotherapy apparatus as recited in claim 18, wherein:

the power supply includes a configuration to charge the capacitor to one of a plurality of predetermined voltages based upon the output voltage from the measuring device.

23. The electrotherapy apparatus as recited in claim 18, wherein:

the controller includes a configuration to perform an interpolation using the output voltage from the measuring device to determine a charge voltage for charging the capacitor with the power supply.

24. The electrotherapy apparatus as recited in claim 23, wherein:

the measuring device includes a second connecting mechanism for coupling and decoupling the measuring device to and from, respectively, the first electrode and the second electrode.

25. A defibrillator for delivering a multi-phasic waveform through a first electrode and a second electrode to a patient for defibrillation, comprising:

a capacitor for storing charge for delivery to the patient through the first electrode and the second electrode with the capacitor having a first terminal and a second terminal;

a power supply for charging the capacitor;

a first connecting mechanism coupled between the first terminal and the second terminal of the capacitor and the first electrode and the second electrode to permit the first terminal of the capacitor to couple and decouple to and from one of the first electrode and the second electrode and to permit the second terminal of the capacitor to couple and decouple to and from one of the first electrode and the second electrode; and a sensor for measuring a first parameter related to the energy supplied by the capacitor;

a circuit to measure a second parameter that varies with patient impedance, with the circuit configured for measuring the second parameter through the first electrode and the second electrode; and a controller coupled to the first connecting mechanism and arranged to receive the first parameter, with the controller configured to actuate the first connecting mechanism to decouple the first terminal and the second terminal of the capacitor from the first electrode and the second electrode based upon the first parameter, with the controller arranged to receive the second parameter from the measuring device and to configure the power supply for charging the capacitor based upon the second parameter.

26. The defibrillator as recited in claim 25, wherein:

the controller includes a configuration to determine a first patient impedance based upon the first parameter, to determine a second patient impedance based upon the second parameter, to determine a difference between the first patient impedance and the second patient impedance, and to configure the power supply for charging the capacitor based upon the difference and the second patient impedance.

27. The defibrillator as recited in claim 26, wherein:

the circuit includes a configuration for performing measurement of the second parameter by applying a waveform having insufficient energy for defibrillation to the patient through the first electrode and the second electrode.

28. The defibrillator as recited in claim 27, wherein:

the controller includes a configuration to configure the power supply for charging the capacitor based upon the sum of the second patient impedance and the difference.

29. The defibrillator as recited in claim 25, wherein:

the circuit includes a signal source for providing a signal through the first electrode and the second electrode for generating the second parameter.

30. The defibrillator as recited in claim 29, wherein:

the first parameter includes a voltage across the capacitor.

31. The defibrillator as recited in claim 29, wherein:

the first parameter includes the charge delivered to the patient.

32. The defibrillator as recited in claim 31, wherein:

the controller includes a configuration to monitor the charge delivered to the patient to determine a time interval for delivering a predetermined amount of charge to the patient and classifying the time interval into one of a plurality of predetermined time intervals, with the controller further including a configuration to select one of a plurality of predetermined time values corresponding to the predetermined time intervals to set a length of time from the coupling of the first terminal and the second terminal to the first electrode and the second electrode to the decoupling of the first terminal and the second terminal from the first electrode and the second electrode.

33. The defibrillator as recited in claim 32, wherein:

the circuit includes a second connecting mechanism for coupling and decoupling the circuit to and from, respectively, the first electrode and the second electrode.

34. The defibrillator as recited in claim 33, wherein:

the second parameter includes a voltage measured across the patient through the first electrode and the second electrode.

* * * * *